United States Patent [19]

Kelly et al.

[11] E Re. 28,913

[45] Reissued July 20, 1976

[54] MILDNESS ADDITIVE

[75] Inventors: Ralph Kelly, Cincinnati; Edmond Jean Ritter, Loveland, both of Ohio

[73] Assignee: Cincinnati Milacron, Inc., Cincinnati, Ohio

[22] Filed: Sept. 17, 1974

[21] Appl. No.: 506,723

Related U.S. Patent Documents

Reissue of:

[64] Patent No.: 3,630,934
Issued: Dec. 28, 1971
Appl. No.: 696,509
Filed: Jan. 9, 1968

U.S. Applications:

[63] Continuation-in-part of Ser. No. 613,095, Feb. 1, 1967, Pat. No. 3,538,009.

[52] U.S. Cl. ..... 252/547; 252/89 R; 252/DIG. 1; 260/407; 424/318; 424/343

[51] Int. Cl.[2] ..... C11D 1/62; C11D 1/66; C11D 3/20

[58] Field of Search ..... 252/547, 108, 110, 152, 252/137, 161, 121, 132, 133, 556, DIG. 1; 260/407, 617 R; 424/318, 343

[56] References Cited

UNITED STATES PATENTS

| | | | |
|---|---|---|---|
| 1,178,142 | 4/1916 | Ellis | 260/407 |
| 2,347,562 | 4/1944 | Johnston | 260/617 |
| 2,411,178 | 11/1946 | Young et al. | 252/57 X |
| 2,673,184 | 3/1954 | Morway et al. | 252/57 X |
| 2,849,399 | 8/1958 | Matuszak et al. | 252/57 X |
| 3,048,542 | 8/1962 | Tierney et al. | 252/57 X |
| 3,157,629 | 11/1964 | Patrick, Jr. | 260/407 X |
| 3,257,377 | 6/1966 | Hannah, Jr. et al. | 260/407 X |
| 3,281,374 | 10/1966 | Walther et al. | 252/309 |
| 3,287,273 | 11/1966 | Furey et al. | 252/57 X |
| 3,472,775 | 10/1969 | Boehringer et al. | 252/57 |
| 3,630,934 | 12/1971 | Kelly et al. | 252/547 |

*Primary Examiner*—Thomas J. Herbert, Jr.
*Attorney, Agent, or Firm*—Plumley and Tyner

[57] ABSTRACT

The degree of skin irritation of detergent compositions is reduced by adding to the detergent compositions small amounts of a hydroxyl derivative of a polymerized fatty acid or a hydroxyl derivative of a hydrogenated (saturated) polymerized fatty acid, e.g. the hydroxy derivative of dimer acid.

12 Claims, No Drawings

MILDNESS ADDITIVE

Matter enclosed in heavy brackets [ ] appears in the original patent but forms no part of this reissue specification; matter printed in italics indicates the additions made by reissue.

*This application is a reissue of U.S. Pat. application Ser. No. 696,509, filed Jan. 9, 1968, now U.S. Pat. 3,630,934 which is a continuation-in-part of U.S. Pat. application Ser. No. 613,095, filed Feb. 1, 1967, now U.S. Pat. 3,538,009 issued Nov. 3, 1970.*

The present invention relates to mildness additives which prevent or reduce skin irritation, to compositions which contain a mildness additive that prevents or reduces skin irritation, and to methods for preventing or reducing skin irritation resulting from contact with irritating compositions by modification of the keratin layer of the skin. [ This application is a continuation-in-part of copending application Ser. No. 613,095, filed Feb. 1, 1967, now U.S. Pat. 3,538,009, issued Nov. 3, 1970.]

A majority of cases of skin irritation can be traced back to a contact of the skin with a chemical composition containing a detergent. This is, in part, due to the nature of the detergent itself and, in part, due to the action of the detergent in weakening the resistance of the skin. Most detergents intrinsically irritate the skin, although the degree of irritation will vary significantly with the detergent. Such irritation can result when the skin is contacted with an aqueous solution of such detergent or when such detergent is retained by a fabric on washing with such detergent which then comes into contact with the skin. As a result of such skin irritation, many otherwise useful detergents are excluded from applications where such detergents come into contact with the skin. In some detergent compositions, e.g. dishwashing liquids and shampoos, a certain degree of skin irritation can be tolerated and is accepted, although not desirable.

The cause for this irritation is not clearly understood, but it is believed that detergents have a denaturing effect on the keratin layer of the skin. As a result thereof, other chemicals which normally do not irritate the skin when combined with a detergent can penetrate the skin and cause irritation. Although numerous attempts have been made to develop additives which reduce or eliminate skin irritation, the additives developed have found only limited success for a very narrow range of detergent compositions.

It is therefore an object of the present invention to prevent or reduce skin irritation resulting from contact of the skin with chemical compositions.

It is another object of the present invention to modify the protein-keratin layer of the skin to prevent or reduce skin irritation when contacted with chemical compositions which irritate the skin.

It is a further object of the present invention to provide modified compositions used in contact with the skin, in which the modification prevents or reduces skin irritation which would otherwise occur.

It is still another object of the present invention to provide detergent-containing compositions to which a mildness additive has been added which prevents or reduces skin irritation which would otherwise result from the presence of such detergent.

Other objects will become apparent from the following description and claims.

The prevention or reduction in skin irritation is achieved by contacting the skin with a mildness additive having the general formula $$Y-R-Y'$$

wherein R is a divalent organic radical containing a chain of at least 15 atoms between the open valences of the radical, the majority of which are carbon atoms, and containing a cyclic moiety of at least 5 atoms, and wherein Y and Y′ are hydroxy groups; said mildness additive being soluble or colloidally dispersible in an aqueous phase or organic solvents or other suitable media; the hydroxy groups of the mildness additive being compatible with those of the irritant and stable in aqueous media. The term "dispersible" is meant to define colloidal dispersibility of the mildness additive in concentrations in which the mildness additive is employed in actual use. The cyclic moiety is preferably a carbocyclic, i.e. cyclic hydrocarbon moiety of 5 to 18 carbon atoms which can be saturated or can contain from 1 to 9 double bonds and can contain one or more substituents on the ring.

In accordance with the present invention, it was discovered that skin irritation and other more severe forms of dermatitis caused by the contact of chemicals with skin can be reduced if not eliminated by contacting the skin with a mildness additive as defined above. This reduction or elimination of skin irritations occurs regardless of whether the mildness additive is applied to the skin prior to or simultaneously with the irritating chemical. Rinsing of the skin with water or a mild soap solution after application of the mildness additive but prior to the application of the irritant does not cause a significant change in the effect of the mildness additive when a skin irritant is subsequently applied. This and other types of evidence, such as electrophoretic studies of mixtures of soluble proteins and mildness additives, have shown that some form of interaction occurs between the keratin layer of the skin and the mildness additive. Although the complex formed between protein molecules and the mildness additive can be isolated by the indicated electrophoresis, the specific nature of the complex has not yet been established. It is presumed, however, that both adsorption and some form of chemical interaction are involved. It is further theorized that the cyclic structure in the mildness additive aids in the adsorption of the additive onto the keratin layer of the skin and that the hydroxy groups of the mildness additive interact with the protein molecules of the keratin layer. In addition to the mildness additive containing at least two hydroxy groups, the hydroxy groups of the mildness additive must also be separated by a chain of at least 15 atoms, a majority of which should be carbon atoms. However, the presence of additional hydroxy groups located intermediary to the described two terminal hydroxy groups does not appear to interfere in the mildness effect of the additive. It is believed that as a result of this chain length, the indicated hydroxy groups are capable and do interact with different protein molecules. The irritation of the skin by the action of a detergent or other irritant is believed to be caused by the penetration of the detergent into the skin, causing separation and/or degradation of the protein molecules of the keratin layer, thereby exposing the living cells of the skin to the detergent and, more significantly, exposing these cells to other, more irritating compounds associated with the detergent. The damage to the cells caused by the contact is believed to result in irritation, inflammation, and dermatitis. The mildness additives employed in the detergent compositions of the present invention are believed to counteract this breakdown by providing additional bridges between the protein molecules of the keratin layer, which maintain the integrity of the skin surface thereby preventing the penetration of the detergent molecules through the keratin layer into the living tissue. It is to be understood, however, that we do not wish to be bound by the foregoing explanation of the activity of the mildness additives of the present invention, and that such explanation is only set forth for a better understanding of the present invention.

The effectiveness of the mildness additive in preventing skin irritation not only requires the presence of at least two hydroxy groups in the mildness additive but also the separation of the hydroxy groups by an atom chain of at least 15 atoms, the majority of which are carbon atoms. The use of shorter chain lengths does not result in a reduction of the irritating effect of a detergent. The presence of additional hydroxy groups does not interfere in the function of the two hydroxy groups separated by the necessary number of atoms, regardless of whether these hydroxy groups are part of such chain or located on side branches of the molecule. The presence of more than two polar groups each of which are separated by 15 or more atoms increases the effectiveness of a mildness additive in which the polar groups are weak polar groups, such as hydroxyl groups, but does not appear to add significantly to the effectiveness of a mildness additive containing at least two strong polar groups such as carboxyl groups separated by the necessary linking chain.

Although the minimum size of the linking radical is determined by the length of the chain separating the hydroxy groups, the maximum size of the linking radical is determined by the dispersibility of the mildness additive in which it is incorporated. Thus compounds which are not liquid or colloidally dispersible are not suitable in preventing skin irritations. Hence, the upper limit of the size of the linking radical is determined not only by the number of atoms in the linking radical, but also by the presence of additional hydroxy groups in the linking radical which can increase the dispersibility of the mildness additive, as well as the nature of any radical attached to the hydroxy group. In general, however, the linking radical contains less than 80 atoms. As indicated, the linking radical has, preferably, a carbon backbone structure which can be aliphatic, cycloaliphatic, or aromatic in nature. The required carbocyclic or heterocyclic moiety need not be part of the backbone structure. Particularly effective are hydrocarbon linking radicals which contain a cycloaliphatic or aromatic ring structure.

Among the preferred mildness additives employed in combination with skin irritants are the hydroxy group containing derivatives of polymerized, ethylenically unsaturated $C_{12}$–$C_{26}$ fatty acids. Generally, the polymerized fatty acids contain from 2 to 4 monomeric acid units, and, consequently, from 2 to 4 carboxyl groups. The polymeric fatty acids can be employed as such as mildness additives or the carboxylic groups can be altered by known chemical reactions into hydroxy groups. The polymerization of ethylenically unsaturated fatty acids into dimer, trimer, and tetramer acids is known in the art and generally results in a cycloaliphatic ring structure. Thus, the dimer acid derived from linoleic acid has the structure, which can exist in the cis and trans forms, of

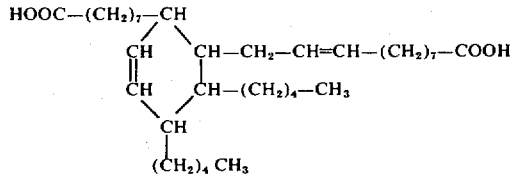

The dimer, trimer, and tetramer acids are commercially available. It will be apparent, in view of the foregoing discussion, that the mildness additive need not be pure, but that a mixture of mildness additives can be employed such as a mixture of dimer and trimer acids, and that the mildness additive can, furthermore, contain compounds which do not add to the mildness properties of the additive such as unpolymerized fatty acids. Hydroxy groups can be substituted for the carboxyl groups of polymerized fatty acids as described above. An example of a suitable mildness additive based on a fatty acid dimer linking radical includes the following in which [D] represets a carboxyl-free residue of dimerized fatty acid:

$$D[CH_2OH]_2$$

The mildness additives described hereinabove can be employed in combination with any detergent that is anionic, cationic, nonionic, or amphoteric in nature. It will be apparent, however, that the hydroxy groups of the mildness additive should be compatible with those of the detergent to avoid insolubilization of both detergent and additive. The reduction of skin irritation will be observable in all compatible combinations, although the extent of the anti-irritant effect will differ with the various mildness additives discussed, as well as with the detergent. Since some of the detergents, particularly nonionic detergents, are by themselves relatively non-irritating, the described mildness additive is less useful, although the mildness effect of the additive can be established when such detergents, which at normally used concentrations cause little or no skin irritation, are tested at high concentrations and/or longer periods of contact with the skin.

The anti-irritation effect of the mildness additive is exhibited over a wide range of proportions of additive to detergent as indicated above. However, optimum results are generally obtained when the ratio of detergent to mildness additive is in the range of 3:1 to 1:3. This preferred range is applicable regardless of whether the detergent is employed in a dilute or concentrated form.

Anionic detergents which are improved by combination with the described mildness additives include both the soap and the non-soap detergents. Examples of such soaps are the sodium, potassium, ammonium, and alkylolammonium salts of higher fatty acids ($C_{10}$ to $C_{26}$). Non-soap anionic detergents with which the described mildness additives are suitably employed include alkyl sulfates, alkyl sulfonates, alkyl benzene sulfonates, alkyl phenyl polyoxyalkylene sulfonates, alkyl glyceryl ether sulfonates, alkyl monoglyceride sulfates, alkyl monoglyceride sulfonates, alkyl polyoxyethylene ether sulfonates, acyl sarcosinates, acyl esters of isothionates, acyl-N-methyl taurides, dialkyl esters of sulfosuccinic acid, and mixtures thereof. In these non-soap detergents, the alkyl or acyl radicals contain from 9 to 20 carbon atoms. As in the soaps, these detergents are employed in the form of sodium, potassium, ammonium, and alkylolammonium salts, as well as similar water-soluble salts. Specific examples include sodium lauryl sulfate, potassium-N-methyl lauroyl tauride, triethanol-ammonium dodecyl sulfonate, potassium polypropylene benzene sulfonate, sodium lauryl sulfonate, dioctyl ester of sodium sulfosumminic acid, sodium salt of lauryl polyoxyethylene sulfate, and sodium salt of tridecylether polyoxyethylene sulfate.

The cationic detergents which can be reduced in their skin irritation by the addition of the mildness additives of the present invention include, in particular, quaternary ammonium salts which contain at least one alkyl group having from 12 to 20 carbon atoms. Although the halide ions are the preferred anions, other suitable anions include acetate, phosphate, sulfate, nitrite, and the like. Specific cationic detergents include distearyl dimethyl ammonium chloride, stearyl dimethyl benzyl ammonium chloride, stearyl trimethyl ammonium chloride, coco dimethyl benzyl ammonium chloride, dicoco dimethyl ammonium chloride, cetyl pyridinium chloride, cetyl trimethyl ammonium bromide, stearyl amine salts that are soluble in water such as stearyl amine acetate and stearyl amine hydrochloride, stearyl dimethyl amine hydrochloride, distearyl amine hydrochloride, alkyl phenoxyethoxyethyl dimethyl ammonium chloride, decyl pyridinium bromide, pyridinium chloride derivative of the acetyl amino ethyl esters of lauric acid, lauryl trimethyl ammonium chloride, decyl amine acetate, lauryl dimethyl ethyl ammonium chloride, the lactic acid and citric acid and other acid salts of stearyl-1-amido-imidazoline with methyl chloride, benzyl chloride, chloroacetic acid and similar compounds, mixtures of the foregoing, and the like.

Amphoteric, also referred to as ampholytic, detergents which can be improved by the addition of the described mildness additives include alkyl-$\beta$-iminodipropionate, alkyl-$\beta$-aminopropionate, fatty imidazolines, betaines, and mixtures thereof. Specific examples of such amphoteric detergents are 1-coco-5-hydroxyethyl-5-carboxymethyl imidazoline, dodecyl-$\beta$-alanine, the inner salt of 2-trimethylamino lauric acid, and N-dodecyl-N,N-dimethyl aminoacetic acid.

As indicated above, the mildness additives of the present invention can also be employed in combination with nonionic detergents, although the beneficial effects of the addition of the mildness additive are less pronounced since nonionic detergents are inherently not as irritating as the above-described detergents. Nonionic detergents include, in particular, the alkylene oxide ethers of phenols, fatty alcohols, and alkyl mercaptans, the alkylene oxide esters of fatty acids, the alkylene oxide ethers of fatty acid amides, the condensation products of ethylene oxide with partial fatty acid esters, and mixtures thereof. The polyoxyalkylene chain in such agents can contain from 5 to 30 alkylene oxide units in which each alkylene unit has from 2 to 3 carbon atoms. Specific examples of nonionic detergents include nonyl phenol polyoxyethylene ether, tridecyl alcohol polyoxyethylene ether, dodecyl mercaptan polyoxyethylene thioether, the lauric ester of polyethylene glycol, the lauric ester of methoxy polyethylene glycol, the lauric ester of sorbitan polyoxyethylene ether, and mixtures thereof.

The mildness additives of the present invention are particularly effective in reducing the irritation caused by such anionic detergents as the alkyl sulfates and sulfonates and the alkyl benzene sulfates and sulfonates, and by such cationic detergents as the described fatty alkyl-containing quaternary ammonium compounds.

Many of the detergents described hereinabove are employed in their commercial applications in combination with builders or other additives, depending on the intended commercial utility of the detergent. The presence of such additives does not affect the ability of the mildness additive to counteract the skin irritation caused by the detergent. As indicated above, it is believed that the skin irritation is caused by the action of the detergent on the skin in causing the keratin of the skin to break down. Although the detergent itself may not be extremely irritating, it allows other materials employed in combination with the detergent which are highly irritating to come in contact with the living tissue of the skin, even though in the absence of the detergent such materials are non-irritating in not being able to break down the keratin of the skin. The mildness additives of the present invention are, therefore, capable of protecting the skin against irritation caused by such additives. Builders employed in commercial detergent formulations are generally alkali salts of weak inorganic acids used alone or in admixtures such as alkali metal, ammonium or substituted ammonium salts of carbonates, borates, phosphates, polyphosphates, bicarbonates, and silicates. Specific examples of such salts are sodium tripolyphosphate, sodium carbonate, sodium tetraborate, sodium pyrophosphate, sodium bicarbonate, potassium bicarbonate, sodium mono- and di-orthophosphate, sodium metasilicate, and mixtures thereof.

The built detergent compositions of the present invention can, furthermore, contain other adjuvants normally employed in detergent compositions such as perfumes, anti-tarnishing agents, anti-redeposition agents, bacteriostatic agents, dyes fluorescers, fabric softeners, oxygen or chlorine bleaches, suds builders, sud depressors, sequestrants, and the like. The inorganic builders or the combination of the builders and the adjuvants described can constitute up to 80% of the built detergent composition, the remainder of the built detergent composition being the detergent and the mildness additive.

The detergent compositions of the present invention include laundry detergents, kitchen detergents, shampoos, industrial detergents, and the like. The use of the mildness additive of the present invention does not affect the effective concentrations of the detergent, and hence concentrations of detergents heretofore employed are also applicable in the modified compositions of the present invention.

The use of the mildness additive is, however, not limited to unbuilt or built detergent compositions. The additive can be employed in any compositions in which a detergent of the type described is employed in the presence of other materials which may cause skin irritation such as, in particular, in lubricants containing inorganic salts, a particular example of which are cutting fluids. The protection against skin irritations is further not limited to detergents and extends to a wide variety of skin irritants, including such as are contained in deodorants, disinfectants, polishes, hair preparations, cleaning compositions, etc. The irritant can be inorganic in nature, or organic. In view of the foregoing explanation, this is not surprising since the protection derived from the mildness additive is based on the interaction of such with the keratin layer of the skin and not on interaction with the irritant. Because of this interaction, it is furthermore unnecessary to combine the mildness additive with the irritant in order to achieve the protection of the skin. Thus, the mildness additive can be applied to the skin prior to any contact with an irritant and will protect the skin against subsequent irritation for a long period of time.

In establishing the irritations and the mildness effect of the additive, the skin is contacted by immersion or other means with a solution containing the irritant with and without the mildness additive under standardized conditions more specifically described below. The principal test employed in the data presented below is an animal immersion test using female, albino guinea pigs. The animals, weighing about 300 to 325 g., is immersed up to the thoracic region in the test solution at 40° C. for 4.5 hours per day on three successive days. Each animal is thoroughly rinsed and dried after each immersion. Three days after the last immersions, the skin of each animal is examined for gross changes, and grades are assigned which represent the degree of damage to the skin. In general, three animals are tested simultaneously in the same solution. The grading system is based on a scale of 1 to 10, in which the numbers have the following meanings:

| Grade or rating | Gross reaction | Skin damage |
|---|---|---|
| 1 | Severe cracking and bleeding; death of animal in most instances. | Extremely severe death of skin tissue. |
| 2 | Severe cracking; moderate bleeding | " |
| 3 | Severe cracking; slight to moderate bleeding. | Severe. |
| 4 | Moderate cracking | " |
| 5 | Slight cracking | Moderate. |
| 6 | Severe scaling | " |
| 7 | Edema; slight to moderate scaling | " |
| 8 | Slight scaling and moderate edema | Slight |
| 9 | Slight redness and edema | " |
| 10 | Normal | Normal. |

Despite the fact that this exposure test is conducted using extremely dilute solutions, it is an exaggerated test, as compared to human exposure; although it has been established (see Canadian Pat. 639,398) that the test correlates extremely well with the skin irritation effect observed on human skin.

In preparing the test solution, a 100 g. concentrate is first prepared which is then employed in the test solution in 1% by volume concentrations. In order to prepare a homogeneous concentrate which is readily dilutable, the following additional ingredients were added as indicated: Igepal CA-630, a commercially available nonionic wetting agent of octylphenoxypoly(oxyethylene)ethanol; triethanol amine, and capric acid. The triethanol amine (TEA) is employed to allow salt formation of mildness additives employed in combination with anionic detergents and the capric acid (Cap. A.) is employed for the same purpose in combination with cationic detergents. In general, the detergent and the mildness additives are each employed in the examples illustrated below in a concentration of 15 weight percent based on the described 100 g. concentrate. Where a built detergent is employed, the amount of detergent is accordingly adjusted to take into consideration the lower active detergent concentration.

The following examples illustrate the effect of the mildness additives of the present invention on skin irritation caused by detergents, using the above-described test.

EXAMPLES 1 TO 12

The detergent employed in this series of tests was an alkyl benzene sulfonate having the formula

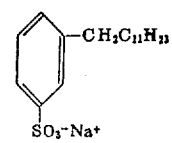

The detergent was employed in 100% active form or in 87% active form, the latter form containing sodium sulfate. The mildness additives employed in this series comprised the dimer of linoleic acid, commercially available as EMPOL 1022, and derivatives of the dimer acid. The dimer acid contained 2–5% of unpolymerized linoleic acid and 19–22% of trimer acid. The dimer ester was prepared from the dimer acid by esterification with a polyethylene glycol having a molecular weight of 400 in a molar ratio of acid-to-polyether of 1:1.25 until an acid number of 5 was obtained. The dimer amide employed is the reaction product of one mole of dimer acid with 4 moles of diethanol amine. The dimer morpholide employed is the reaction product of 4 moles of morpholine with one mole of dimer acid. The dimer amine employed is a commmercially available compound in which the carboxyl groups of the dimer acid are replaced by amino methyl ($-CH_2NH_2$) groups. Table I illustrates the results obtained employing the above-described test. The actual composition of the solution to which the animals were exposed is shown. The remainder of the composition of the test solution not indicated in the table was water.

TABLE I

ALKYL BENZENE SULFONATE EXPOSURE

| Example No. | Detergent: Percent concentration | Detergent: Percent active | Dimer additive: Type | Dimer additive: Percent concentration | Other Additive: Type | Other Additive: Percent concentration | Average rating | Improvement in rating | Ratio of detergent to mildness additive |
|---|---|---|---|---|---|---|---|---|---|
| 1 | 0.15 | 87 | | | Igepal | 0.05 | 4 | | |
| 2 | 0.15 | 87 | Acid | 0.15 | Igepal<br>TEA | 0.016<br>0.034 | 9 | 5 | 1:1 |
| 3 | 0.15 | 87 | Ester | 0.15 | Igepal | 0.05 | 8+ | 4+ | 1:1 |
| 4 | 0.15 | 87 | Amide | 0.15 | Igepal | 0.05 | 9 | 5 | 1:1 |
| 5 | 0.15 | | | | | | Death | | |
| 6 | 0.15 | 87 | Acid | 0.15 | TEA | 0.10 | 7+ | 7+ | 1:1 |

TABLE I-continued

| | ALKYL BENZENE SULFONATE EXPOSURE | | | | | | | | |
|---|---|---|---|---|---|---|---|---|---|
| | Detergent | | Dimer additive | | Other Additive | | | | |
| Example No. | Percent concentration | Percent active | Type | Percent concentration | Type | Percent concentration | Average rating | Improvement in rating | Ratio of detergent to mildness additive |
| 7 | 0.176 | 100 | | | | | Death | | |
| 8 | 0.176 | 100 | Acid | 0.15 | TEA | 0.10 | 8 | 8 | 1:1 |
| 9 | 0.176 | 100 | Ester | 0.15 | | | 8+ | 8+ | 1:1 |
| 10 | 0.176 | 100 | Amide | 0.15 | | | 9 | 9 | 1:1 |
| 11 | 0.176 | 100 | Morph | 0.15 | TEA | 0.05 | 8+ | 8+ | 1:1 |
| 12 | 0.15 | 87 | Diamine | 0.15 | Igepal<br>Cap. A | 0.10<br>0.15 | 9 | 5 | 1:1 |

EXAMPLES 13 TO 32

The tests and determination of results illustrated in Examples 1–12 were repeated using sodium lauryl sulfate instead of the alkyl benzene sulfonate. The results are illustrated in Table II.

TABLE II

| | SODIUM LAURYL SULFATE EXPOSURE | | | | | | | | |
|---|---|---|---|---|---|---|---|---|---|
| | Detergent | | Dimer additive | | Other additive | | | | |
| Example No. | Percent concentration | Percent active | Type | Percent concentration | Type | Percent concentration | Average rating | Improvement in rating | Ratio of detergent to mildness additive |
| 13 | 0.15 | 100 | | | Igepal | 0.05 | 3 | | |
| 14 | 0.15 | 100 | Acid | 0.15 | Igepal<br>TEA | 0.016<br>0.034 | 7 | 4 | 1:1 |
| 15 | 0.15 | 100 | Ester | 0.15 | Igepal | 0.05 | 8– | 5– | 1:1 |
| 16 | 0.15 | 100 | Amide | 0.15 | Igepal | 0.05 | 7 | 4 | 1:1 |

EXAMPLES 17–18

The tests and determination of results illustrated in Examples 1–12 and 13–16 were repeated using a dimer glycol. The following results were obtained:

| Example | Detergent | Mildness additive | Average rating |
|---|---|---|---|
| 17 | Alkylbenzene | Dimer glycol D—$[CH_2OH]_2$ | 8 |
| 18 | Sodium lauryl sulfate. | Dimer glycol | 7+ |

The foregoing examples have illustrated the mildness inducing effect of the mildness additives on the keratin layer of the skin when such is exposed to a skin irritant. In many detergent-containing compositions the skin irritation caused by the detergent is compounded by detergent builders or other components present in the composition. The foregoing examples clearly demonstrate that the mildness agents employed in combination with the detergents are particularly effective in reducing skin irritation where the skin irritation is compounded by the presence of other agents, organic or inorganic. In view of the fact that the overall chemical structure of the mildness additives of the present invention is similar to that of a detergent, it will be apparent that the mildness additives of the present invention can be employed in combination with a skin irritating detergent in any environment, i.e. in the presence of any component in which the detergent can exist. The foregoing examples further illustrate that the greatest benefit of the described invention is realized when the mildness additives are combined with detergents or with detergent-containing compositions which cause skin irritation.

In view of the extreme diversity of skin irritants known today, it will be apparent that a demonstration of reduced skin irritation of all detergent compositions with the described mildness additives is not possible. However, such is not deemed necessary and the foregoing examples are deemed sufficient to illustrate the scope of the invention but are not intended to limit the scope of the invention to such.

What is claimed is:

1. A detergent composition consisting essentially of a skin irritating detergent selected from the group consisting of [ anionic, ] cationic, non-ionic, and amphoteric organic detergents and .005 to 10 parts by weight based on said skin irritating detergent of a mildness additive comprising (I) the substituted polymerized product of 2 to 4 molecules of a monomeric $C_{12}$ to $C_{26}$ fatty acid, wherein said product contains a cyclohexene moiety and instead of 2 to 4 carboxyl groups from said fatty acid, hydroxy or hydroxy methyl groups; or (II) the substituted saturated polymerized product defined in (I);

said detergent composition exhibiting reduced skin irritation compared to the same composition absent the mildness additive; the mildness additive and detergent composition being stable and compatible in aqueous media.

2. The detergent composition of claim 1 wherein said mildness additive is selected from the group designated (I).

3. The composition of claim 1 wherein said mildness [ additives ] *additive* is defined as (I) and contains hydroxy methyl groups.

4. The composition of claim 1 wherein said mildness additive is selected from the group designated (II).

5. The composition of claim 1 wherein said mildness additive is the glycol derivative of the polymerization product of 2 to 4 mols of linoleic acid.

6. The composition of claim 5 wherein said mildness additive is the glycol of the dimer of linoleic acid.

7. The composition of claim 1 wherein the weight ratio of mildness additive to detergent is from 0.33 to 3.

[ 8. The composition of claim 1 wherein the detergent is an anionic detergent. ]

[ 9. The composition of claim 1 wherein the anionic detergent is alkyl benzene sulfonate, alkyl sulfate, alkyl benzene sulfates, or alkyl sulfonate. ]

10. The composition of claim 1 wherein the detergent is a cationic detergent.

11. The composition of claim 1 wherein the cationic detergent is a quaternary ammonium compound.

12. The composition of claim 1 wherein the detergent is an amphoteric detergent.

13. The composition of claim 1 wherein the amphoteric detergent is an alkyl-$\beta$-imino propionate.

14. The composition of claim 1 wherein the detergent composition contains from 10 to 80% by weight of the composition of water soluble inorganic detergent builders.

* * * * *